United States Patent [19]

Schuster et al.

[11] Patent Number: 5,101,044
[45] Date of Patent: Mar. 31, 1992

[54] PREPARATION OF N-SUBSTITUTED PYRROLIDIN-2-ONES

[75] Inventors: Ludwig Schuster, Limburgerhof; Ulrich Koehler, Heidelberg, both of Fed. Rep. of Germany

[73] Assignee: BASF Aktiengesellschaft, Ludwigshafen, Fed. Rep. of Germany

[21] Appl. No.: 577,589

[22] Filed: Sep. 4, 1990

[30] Foreign Application Priority Data

Sep. 1, 1989 [DE] Fed. Rep. of Germany ....... 3928981
Sep. 1, 1989 [DE] Fed. Rep. of Germany ....... 3928982

[51] Int. Cl.$^5$ ................ C07D 207/267; C07D 207/36
[52] U.S. Cl. ..................................... 548/543; 548/550; 548/552
[58] Field of Search ................ 548/543, 552, 553, 550

[56] References Cited

U.S. PATENT DOCUMENTS 4,962,204 10/1990 Wambach ........................ 548/543

FOREIGN PATENT DOCUMENTS 604321 8/1960 Canada ................................ 548/553

OTHER PUBLICATIONS

Weissermel, Arpe: Industrielle Organische Chemie, (1988), pp. 105–109.

*Primary Examiner*—Mary C. Lee
*Assistant Examiner*—Lenora A. Miltenberger
*Attorney, Agent, or Firm*—John H. Shurtleff

[57] ABSTRACT

A process for the preparation of N-substituted pyrrolidin-2-ones of the general formula I

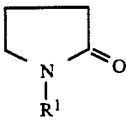

where $R^1$ is $C_1$- to $C_{20}$-alkyl, $C_6$- to $C_{10}$aryl or $C_7$- to $C_{12}$-aralkyl comprises hydrogenolytically cleaving 5-iminopyrrolidin-2-ones of the general formula II

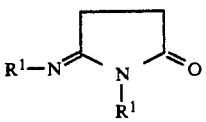

in which the $R^1$ radicals are identical or different $C_1$- to $C_{20}$-alkyl, $C_6$- to $C_{10}$-aryl or $C_7$- to $C_{12}$-aralkyl, at superatmospheric pressure and elevated temperature in the presence of a hydrogenation catalyst to give the pyrrolidin-2-ones I; specifically, the 5-iminopyrrolidin-2-ones of the formula II are obtained by reacting $\beta$-cyanopropionic acid esters of the general formula III

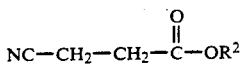

where $R^2$ is $C_1$- to $C_{20}$-alkyl, $C_7$- to $C_{12}$-aralkyl or $C_6$- to $C_{10}$-aryl, with an amine of the general formula IV $$R^1-NH_2 \qquad \text{IV}$$

where $R^1$ is as defined above.

15 Claims, No Drawings

PREPARATION OF N-SUBSTITUTED PYRROLIDIN-2-ONES

The present invention relates to a process for the preparation of N-substituted pyrrolidin-2-ones from N,N'-disubstituted 5-iminopyrrolidin-2-ones on hydrogenation catalysts at elevated pressure and temperature.

N-Substituted pyrrolidin-2-ones, in particular N-methylpyrrolidone (NMP) of the formula III

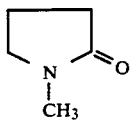

can be obtained on an industrial scale by reacting butyrolactone with the relevant primary amine, in particular methylamine. This process has proven successful, in particular, for the preparation of NMP. Butyrolactone is prepared by catalytic dehydrogenation of 1,4-butanediol, the preparation of which is based, for example, on the feedstock acetylene (in this respect, cf. Weissermel, Arpe: Industrielle organische Chemie, pages 105 to 109, VCH-Verlagsgesellschaft, Weinheim 1988).

Since the competitivity of processes for the preparation of large-scale chemical products is highly dependent on the prices of the feedstocks required, which in turn can vary considerably from time to time and from place to place depending on the availability on the world market and on the existence of feedstock sources and chemical plants for producing them inexpensively, it is an object of the present invention to find an economical process for the preparation of N-substituted pyrrolidin-2-ones which is based on an alternative feedstock to acetylene.

We have found that this object is achieved by a novel and improved process for the preparation of N-substituted pyrrolidin-2-ones of the general formula I

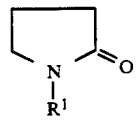

where $R^1$ is $C_1$- to $C_{20}$-alkyl, $C_6$- to $C_{10}$-aryl or $C_7$- to $C_{12}$-aralkyl, which comprises hydrogenolytically cleaving 5-iminopyrrolidin-2-ones of the general formula II

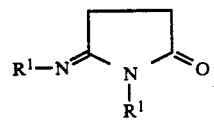

where the $R^1$ radicals may be identical or different $C_1$- to $C_{20}$-alkyl, $C_6$- to $C_{10}$-aryl or $C_7$- to $C_{12}$-aralkyl, at superatmospheric pressure and elevated temperature in the presence of a hydrogenation catalyst to give the pyrrolidin-2-ones I. Specifically, 5-iminopyrrolidones of the formula II can be obtained by reacting β-cyanopropionic acid esters of the general formula III

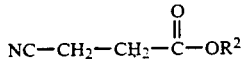

where $R^2$ is $C_1$- to $C_{20}$-alkyl, $C_7$- to $C_{12}$-aralkyl or $C_6$- to $C_{10}$-aryl, with an amine of the general formula IV

in which $R^1$ is as defined above.

Preparation of the 5-iminopyrrolidin-2-ones of the general formula II

The β-cyanopropionic acid esters III used as starting compounds can be obtained in virtually quantitative yield by the addition reaction of hydrocyanic acid with the appropriate acrylic acid ester. The number of reaction steps for the preparation of the compound III is thus reduced to 2, as can be seen from the scheme below.

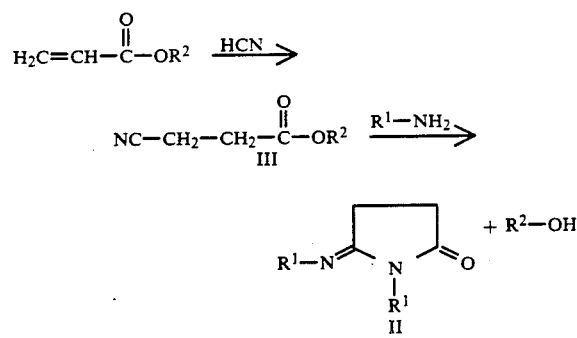

The nature of the ester component $R^2$ in the β-cyanopropionic acid ester III is of only minor significance for the success of the process according to the invention, and $R^2$ can thus be, for example, $C_1$- to $C_{20}$-alkyl, $C_7$- to $C_{12}$-aralkyl or $C_6$- to $C_{10}$-aryl. Of course, $R^2$ should not be so bulky as to cause steric hindrance in the reaction. However, β-cyanopropionic acid esters III in which $R^2$ is $C_1$- to $C_4$-alkyl are preferred due to their ready accessibility and favorable price. $R^2$ may of course also be substituted by substituents which are inert under the reaction conditions.

The nature of $R^1$ in the compounds II is naturally dependent on the type of amines IV ($R^1$—$NH_2$) used for cyclizing the β-cyanopropionic acid esters III, for which purpose virtually any primary amine $R^1$—$NH_2$ is suitable, i.e. any amine in which $R^1$ is an aliphatic radical having from 1 to 20 carbon atoms, an aromatic radical having from 6 to 10 carbon atoms or an araliphatic radical having from 7 to 12 carbon atoms, provided that the $R^1$ radicals are not so bulky as to cause steric hindrance in the reaction. Accordingly, amines IV in which $R^1$ is $C_1$- to $C_{20}$-alkyl, $C_6$- to $C_{10}$-aryl or $C_7$- to $C_{12}$-aralkyl can be used. In addition, amines IV which contain hetero atoms such as oxygen, nitrogen or sulfur in their aliphatic, cycloaliphatic, aromatic or araliphatic radical can be used. Preferred amines IV are those in which $R^1$ is $C_1$- to $C_4$-alkyl, particularly preferably methyl. It goes without saying that the use of amines IV in which $R^1$ is substituted by substituents which are inert under the reaction conditions has no adverse effect on the success of the process. Examples of such substituents are ether groups or acetal groups.

The β-cyanopropionic acid ester III is usually reacted with only one amine species $R^1$—$NH_2$. It is of course also possible to react this ester with a mixture of amines $R^1$—$NH_2$ with different radicals $R^1$, which gives product mixtures containing compounds II in which the radicals $R^1$ are different.

In the process according to the invention, the amines IV can be employed, based on the β-cyanopropionic acid ester III, either in a stoiciometric amount, i.e. 2 mol of amine IV/mole of ester III, or in excess. It is expedient to use an excess of the amine IV, with from 2.2 to 10 mol, preferably from 2.5 to 4 mol, of amine IV being employed per mole of ester III.

The reaction of the amine IV with the β-cyanopropionic acid ester III can be carried out in a solvent which is inert under the reaction conditions, such as tetrahydrofuran or dioxane. However, the reaction is preferably carried out in the absence of an additional solvent, but the amine III added in excess or the product I added may also serve as the solvent. A particular case where solvents are added to the reaction batch is when the starting materials and/or product I are solids.

The reaction can be carried out either at atmospheric pressure or at superatmospheric pressure. Superatmospheric pressure, in particular autogenous pressure, is expediently used in cases where one of the reactants, generally the amine IV, boils under the reaction conditions. It is also possible to pass a reactant which is gaseous under the reaction conditions, for example methylamine, in gas form and atmospheric pressure into the liquid reaction mixture.

The two reactants β-cyanopropionic acid ester III and the amine IV can react with one another even at room temperature. In order to accelerate and complete the reaction, however, elevated temperatures are generally used. The reaction is expediently carried out at from 20° to 250° C., preferably form 30° to 150° C., in particular from 90° to 130° C. As stated above, the reaction is expediently carried out under the autogenous pressure generated by the reactants at these temperatures. A further exogenous increase in the reaction pressure is possible, but is generally not necessary.

The 5-iminopyrrolidin-2-ones II can be isolated in high purity from the reaction products in a conventional manner, for example by distillation or crystallization. The alcohol $R^2OH$ liberated during the reaction can be recovered by distillation and re-used.

As required, the process according to the invention can be carried out batchwise or continuously. The reactors usually used for these procedures can be employed—for example stirred or bubble reactors for the continuous procedure.

The hydrogenolytic cleavage of the 5-iminopyrrolidin-2-ones of the general formula II proceeds formallin in accordance with the reaction equation below:

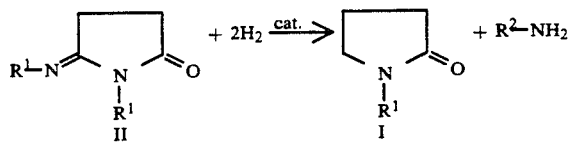

The process according to the invention is advantageous for the preparation of N-substituted pyrrolidin-2-ones in which $R^1$ is $C_1$- to $C_{20}$-alkyl, $C_6$- to $C_{10}$-aryl or $C_7$- to $C_{12}$-aralkyl, and particularly preferably allows the preparation of N-substituted pyrrolidin-2-ones in which $R^1$ is $C_1$ to $C_4$-alkyl and in particular methyl.

The starting materials for the preparation of N-substituted pyrrolidin-2-ones I are 5-iminopyrrolidin-2-ones III which the imido nitrogen carries the appropriate radical $R^1$ and in which the imino nitrogen may also be substituted or may carry a $C_1$- to $C_{20}$-alkyl, $C_6$- to $C_{10}$-aryl or $C_7$- to $C_{12}$-aralkyl group. $R^1$ in II may be identical or different. Preferred compounds II are those in which the radicals $R^1$ are identical $C_1$- to $C_4$-alkyl groups, in particular methyl groups.

In principle, all hydrogenation catalysts are suitable for the hydrogenolytic removal of the imino group from the 5-iminopyrrolidin-2-ones II, i.e. of the large number of hydrogenation catalysts tested, none has hitherto been found with which the reaction according to the invention cannot be carried out. Examples of suitable hydrogenation catalysts are platinum metals, such as platinum, palladium, rhodium and ruthenium, and the oxides and oxide hydrates thereof, Raney nickel, Raney cobalt, Raney copper, iron or iron(III) oxide. These hydrogenation catalysts can be used as such in pure form, preferably in finely divided form having a large surface area, or, advantageously, deposited on an inert carrier material, i.e. as supported catalysts, on any carrier material which has proven successful for hydrogenation catalysts, such as alumina, zirconium dioxide, barium sulfate or activated charcoal.

It is of course also possible to use mixed catalysts as the hydrogenation catalysts in the process according to the invention. Examples of these are the hydrogenation catalysts of German Patent 1,235,879 or chromite-based hydrogenation/dehydrogenation catalysts (see, for example, U.S. Pat. Nos. 2,492,614; 1,977,750; J. Amer. Chem. Soc. 62, (1940), 2874 to 2876).

The hydrogenation is advantageously carried out at superatmospheric pressure and at elevated temperature. In general, the reaction according to the invention is carried out at from 150° to 250° C., preferably from 170° to 220° C., in particular from 180° to 200° C., and at from 100 to 400 bar, advantageously from 200 to 350 bar, particularly preferably from 250 to 320 bar.

The hydrogenation can be carried out in the presence or absence of solvents which are inert under the reaction conditions, such as tetrahydrofuran, dioxane, dimethoxyethane, hydrocarbons or aliphatic alcohols. The addition of a solvent to the reaction batch may be particularly advantageous if the starting material and/or the product is a solid at room temperature.

If required, the reaction according to the invention can be carried out batchwise in a stirred autoclave using a suspended catalyst or continuously in a fixed-bed reactor, either using a liquid phase or trickle-bed procedure. The pyrrolidin-2-ones I are generally isolated by cooling and decompressing the reaction products, separating off the catalyst if necessary, and purifying the product by distillation or crystallization.

The process according to the invention allows N-substituted pyrrolidin-2-ones I to be obtained competitively and in high purity from an alternative feedstock source.

The N-substituted pyrrolidin-2-ones I obtainable by the process according to the invention can be used, for example, in a wide range of solvent and extractant applications.

EXAMPLES

EXAMPLE 1

350 g of methyl β-cyanopropionate were introduced at room temperature into an autoclave, and 350 g of gaseous methylamine were injected. After the initial reaction had subsided, the mixture was heated at 130° C. for 3 hours, a pressure of 20 bar being produced in the autoclave. The reaction products were subjected to fractional distillation under reduced pressure. 1-Methyl-5-methylimino-2-pyrrolidone was obtained in a yield of 98%, based on the ester II, and in a purity of 99.2%.

EXAMPLE 2

The following were introduced into a 300 ml capacity autoclave:
- 30 g of 5-N-methylimino-N-methyl-2-pyrrolidone,
- 130 g of tetrahydrofuran and
- 2 g of catalyst (palladium on alumina carrier; palladium content: 5% by weight).

100 bar of hydrogen were injected at room temperature, and the autoclave was heated to 180° C. with stirring, whereupon the pressure was increased to 300 bar by injecting hydrogen. After 5 hours, the mixture was cooled and decompressed, the catalyst was filtered off, and the products were worked up by distillation, to give 19 g of N-methylpyrrolidone (yield: 81%).

EXAMPLE 3

Example 2 was repeated using the following starting materials:
- 80 g of 5-N-methylimino-N-methyl-2pyrrolidone,
- 80 g of tetrahydrofuran and
- 5 g of Raney copper.
- 38 g of NMP were obtained (yield: 61.5%).

EXAMPLE 4

Example 2 was repeated using the following starting materials:
- 80 g of 5-N-methylimino-N-methyl-2-pyrrolidone,
- 80 g of tetrahydrofuran and
- 5 g of catalyst as in German Patent 1,235,879 (composition: 20% by weight of cobalt, 55% by weight of copper and 25% by weight of manganese).
- 41 g of NMP were obtained (yield: 65%).

EXAMPLE 5

Example 2 was repeated using the following starting materials:
- 80 g of 5-N-methylimino-N-methyl-2-pyrrolidone,
- 80 g of tetrahydrofuran and
- 5 g of Raney nickel.
- 38 g of NMP were obtained (yield: 61.5%).

We claim:

1. A process for the preparation of an N-substituted pyrrolidin-2-one of the formula I

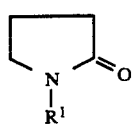

where $R^1$ is $C_1$- to $C_{20}$-alkyl, $C_6$- to $C_{10}$-aryl or $C_7$- to $C_{12}$-aralkyl, which comprises hydrogenolytically cleaving a 5-iminopyrrolidin-2-one of the formula II

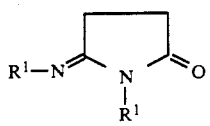

where the $R^1$ radicals may be identical or different $C_1$- to $C_{20}$-alkyl, $C_6$- to $C_{10}$-aryl or $C_7$- to $C_{12}$-aralkyl, at superatmospheric pressure and elevated temperature in the presence of a hydrogenation catalyst to give a pyrrolidin-2-one I.

2. A process for the preparation of an N-substituted pyrrolidin-2-one of the formula I

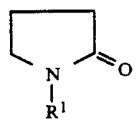

where $R^1$ is $C_1$- to $C_{20}$-alkyl, $C_6$- to $C_{10}$-aryl or $C_7$- to $C_{12}$-aralkyl, which comprises reacting a β-cyanopropionic acid ester of the formula III

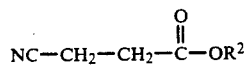

where $R^2$ is $C_1$- to $C_{20}$-alkyl, $C_7$- to $C_6$- to $C_{10}$-aryl, with an amine of the formula IV

where $R^1$ is as defined above, and then isolating and hydrogenolytically cleaving the resultant 5-iminopyrrolidin-2-one of the formula II

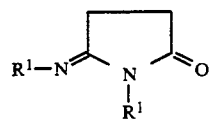

where the $R^1$ radicals may be identical or different $C_1$- to $C_{20}$-alkyl, $C_6$- to $C_{10}$-aryl or $C_7$- to $C_{12}$-aralkyl, at superatmospheric pressure and at elevated temperature in the presence of a hydrogenation catalyst to give a pyrrolidin-2-one I.

3. A process as claimed in claim 1, wherein $R^1$ in formula II, each occurrence, is $C_1$- to $C_4$-alkyl.

4. A process as claimed in claim 2, wherein $R^1$ in formulas II and IV, each occurrence, is $C_1$- to $C_4$-alkyl.

5. A process as claimed in claim 1, wherein the hydrogenolytic cleavage of the compound II is carried out at from 150° to 250° C. and at from 100 to 400 bar.

6. A process as claimed in claim 1, wherein the hydrogenolytic cleavage of the compound II is carried out at from 170° to 220° and at from 200 to 350 bar.

7. A process as claimed in claim 2, wherein the reaction of the ester III with the amine IV is carried out at a temperature of from 20° to 250° C. under the autogenous pressure of the reactants at such temperatures.

8. A process as claimed in claim 2, wherein the reaction of the ester III with the amine IV is carried out at a temperature of from 30° to 150° C. under the autogenous pressure of the reactants at such temperatures.

9. A process as claimed in claim 2, wherein the reaction of the ester III with the amine IV is carried out at a temperature of from 90° to 130° C. under the autogenous pressure of the reactants at such temperatures.

10. A process as claimed in claim 2, wherein the 5-iminopyrrolidin-2-one II is first separated and isolated from the reaction mixture prior to its hydrogenolytic cleavage by cooling and decompressing the reaction products, separating off any catalyst and then purifying the product.

11. A process as claimed in claim 2, wherein the amine IV is used in at least a stoichiometric amount with reference to the ester III.

12. A process as claimed in claim 2, wherein the amine IV is used in an amount of 2.2 to 10 moles per mole of the ester III.

13. A process for the preparation of a 5-iminopyrrolidin-2-one of the formula

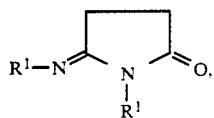

where the $R^1$ radicals may be identical or different $C_1$- to $C_{20}$-alkyl, $C_6$ to $C_{10}$-aryl or $C_7$- to $C_{12}$-aralkyl, which comprises:

reacting a β-cyanopropionic acid ester of the formula

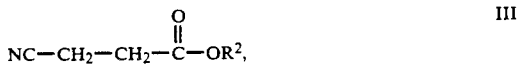

where $R^2$ is $C_1$- to $C_{20}$-alkyl, $C_6$- to $C_{10}$-aryl or $C_7$-$C_{12}$-aralkyl, with at least one amine of the formula

where $R^1$ is as defined above, at from about 20° to 250° C., and isolating and purifying the product II by at least one of the steps of distillation and crystallization.

14. A process as claimed in claim 13, wherein the reaction of III and IV is carried out at a temperature of 30° to 150° C.

15. A process as claimed in claim 13, wherein the reaction of III and IV is carried out at a temperature of 90° to 130° C. and under autogenous pressure.

* * * * *

UNITED STATES PATENT AND TRADEMARK OFFICE
CERTIFICATE OF CORRECTION

PATENT NO. : 5,101,044
DATED : March 31, 1992
INVENTOR(S) : Schuster et al

It is certified that error appears in the above-identified patent and that said Letters Patent is hereby corrected as shown below:

Col. 6, line 2; in the first line following the formula III: after "C7- to", insert -- $C_{12}$-aralkyl or --.

Col. 6, line 6, line 3: after "220°", insert -- C. --.

Signed and Sealed this

Fifteenth Day of June, 1993

Attest:

MICHAEL K. KIRK

*Attesting Officer*      Acting Commissioner of Patents and Trademarks